United States Patent
Lang et al.

(10) Patent No.: US 10,730,823 B2
(45) Date of Patent: *Aug. 4, 2020

(54) PROCESS FOR ISOLATING PURE TERT-BUTYL (METH)ACRYLATE FROM CRUDE TERT-BUTYL (METH)ACRYLATE BY DISTILLATION

(71) Applicant: BASF SE, Ludwigshafen am Rhein (DE)

(72) Inventors: Ortmund Lang, Ludwigshafen (DE); Bernd Metzen, Ludwigshafen (DE); Claus Hechler, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/471,993

(22) PCT Filed: Dec. 11, 2017

(86) PCT No.: PCT/EP2017/082193
§ 371 (c)(1),
(2) Date: Jun. 20, 2019

(87) PCT Pub. No.: WO2018/114425
PCT Pub. Date: Jun. 28, 2018

(65) Prior Publication Data
US 2019/0330137 A1 Oct. 31, 2019

(30) Foreign Application Priority Data

Dec. 21, 2016 (EP) ..................................... 16205961

(51) Int. Cl.
| C07C 67/54 | (2006.01) |
| C07C 69/54 | (2006.01) |
| B01D 3/14 | (2006.01) |
| B01D 3/22 | (2006.01) |

(52) U.S. Cl.
CPC .............. *C07C 67/54* (2013.01); *B01D 3/141* (2013.01); *B01D 3/225* (2013.01); *C07C 69/54* (2013.01)

(58) Field of Classification Search
CPC ......... C07C 67/54; C07C 69/54; B01D 3/225; B01D 3/141
See application file for complete search history.

(56) References Cited

U.S. PATENT DOCUMENTS 8,530,700 B2 * 9/2013 Ho ........................... C07C 51/44
562/545

8,894,821 B2 * 11/2014 Lee ........................ B01D 3/141
202/158

2013/0284586 A1 10/2013 Lee et al.
2019/0016665 A1 1/2019 Tretjak et al.

FOREIGN PATENT DOCUMENTS

| DE | 33 02 525 A1 | 7/1984 | |
| DE | 102 58 329 A1 | 7/2003 | |
| DE | 10 2005 053 982 A1 | 5/2006 | |
| JP | 2005-239564 A | 9/2005 | |
| JP | 2005239564 A * | 9/2005 | ............. C07C 67/54 |
| WO | WO 02/10110 A2 | 2/2002 | |
| WO | WO 03/043712 A1 | 5/2003 | |
| WO | WO 2017/125657 A1 | 7/2017 | |

OTHER PUBLICATIONS

Arjomand (Scientia Iranica C, Optimal operation of a divided-wall column with local operating condition changes, 2015, 22(6), pp. 2358-2372. (Year: 2015).*
U.S. Appl. No. 16/062,369, filed Jun. 14, 2018, US 2019-0002389 A1, Horstmann, C., et al.
U.S. Appl. No. 15/086,715, filed Mar. 31, 2016, US 2016-0289159 A1, Horstmann, C., et al.
U.S. Appl. No. 15/741,350, filed Jan. 2, 2018, US 2018-0361270 A1, Asprion, N., et al.
U.S. Appl. No. 16/472,018, filed Jun. 20, 2019, Lang, O., et al.
U.S. Appl. No. 16/468,823, filed Jun. 12, 2019, Lang, O., et al.
U.S. Appl. No. 16/471,993, filed Jun. 20, 2019, Lang, O., et al.
U.S. Appl. No. 16/472,054, filed Jun. 20, 2019, Lang, O., et al.
Extended European Search Report dated Jun. 26, 2017 in European Patent Application No. 16205961.2 (with English translation of Category of Cited Documents), 4 pages.
Kaibel, G., "Distillation columns with vertical partitions", Chemical Engineering and Technology, vol. 10, Issue 1, 1987, pp. 92-98.
Kaibel, G., et al., "Möglichkeiten zur Prozeßintegration bei destillativen Trennverfahren", Chemie Ingenieur Technik, vol. 61, Issue 2, Feb. 27, 1989, pp. 104-112.
International Search Report dated on Mar. 26, 2018, in PCT/EP2017/082193 filed Dec. 11, 2017.

* cited by examiner

*Primary Examiner* — Paul A Zucker
(74) *Attorney, Agent, or Firm* — Oblon, McClelland, Maier & Neustadt, L.L.P.

(57) ABSTRACT

A process for isolating pure tert-butyl (meth)acrylate from crude tert-butyl (meth)acrylate by distillation, wherein the process is carried out in a dividing wall column having separation-active internals and a vaporizer and in which a dividing wall is arranged in the longitudinal direction of the column to form an upper joint column region, a lower joint column region, an inflow section having a side feed point, and an offtake section having a side offtake point, where the column has from 20-80 theoretical plates and the ratio of the amount of liquid at the upper end of the dividing wall going to the enrichment section and the stripping section of the column is set in the range from 1:0.2 to 1:5.

22 Claims, 2 Drawing Sheets

PROCESS FOR ISOLATING PURE TERT-BUTYL (METH)ACRYLATE FROM CRUDE TERT-BUTYL (METH)ACRYLATE BY DISTILLATION

CROSS-REFERENCE TO RELATED APPLICATIONS

The present application is a 35 U.S.C. § 371 national stage patent application of International patent application PCT/EP2017/082193, filed on Dec. 11, 2017, the text of which is incorporated by reference, and claims the benefit of the filing date of EP application no. 16205961.2, filed on Dec. 21, 2016, the text of which is also incorporated by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT Not Applicable

INCORPORATION-BY-REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

BACKGROUND OF THE INVENTION

Field of the Invention

Esters of (meth)acrylic acid, $H_2C=CH-C(=O)OR$ or $H_2C=C(CH_3)-C(=O)OR$, will hereinafter also be referred to as acrylates. R is an alkyl radical.

tert-Butyl (meth)acrylate, R in the formulae therefore tert-butyl, is obtained by reaction of isobutene with (meth) acrylic acid. The synthesis forms a product mixture, also referred to as crude tert-butyl (meth)acrylate, in which the acrylate generally predominates.

tert-Butyl (meth)acrylates are employed for surface coatings, adhesives, building chemicals, paper coatings and plastics.

Description of the Related Art Including Information Disclosed Under 37 CFR 1.97 and 1.98

In order to meet specification requirements, the crude acrylate obtained in a synthesis has to be purified further by distillation. The specification requirements for pure acrylates provide in particular for, for example, a minimum content of acrylate of 99.5% by weight and a maximum permissible content of acetate, $RO(C=O)CH_3$, of 1500 ppm.

The isolation of acrylate from the crude acrylate is a complicated distillation problem because of the small differences in the relative volatilities of the components and is therefore generally carried out by means of a two-column arrangement. Owing to the sensitivity of the polymerization-prone acrylates, particular column internals are generally particularly advantageous.

The introduction of WO 2002/10110 A2 (BASF AG) (pages 2 to 3) describes the problems and challenges of the isolation of pure tert-butyl (meth)acrylate and teaches a two-stage distillation, with the catalyst originating from the synthesis (reaction of (meth)acrylic acid with isobutene) initially being removed as residue and the pure tert-butyl (meth)acrylate being obtained from the distillates (in particular page 5, line 43, to page 16).

DE 3302525 A1 (BASF AG) and the specialist literature, for example Kaibel et al. in Chem. Eng. Technol. 10 (1987), pages 92 to 98, and in Chem. Ing.-Tech. 61 (1989), No. 2, pages 104 to 112, describe in general terms the use of dividing wall columns in the purification of organic compounds by distillation.

US 2013/0284586 A1 (LG Chem. Ltd.) describes the use of a dividing wall column for purifying 2-ethylhexyl acrylate by distillation.

JP 2005/239564 A (Mitsubishi Rayon Co.) describes the distillation of (meth)acrylic esters using a dividing wall column.

BRIEF SUMMARY OF THE INVENTION

In the light of this literature, it was an object of the invention to provide an improved process for the isolation of pure tert-butyl (meth)acrylate from the corresponding crude tert-butyl (meth)acrylate by distillation, which process is, while adhering to the respective specifications for the pure tert-butyl (meth)acrylate, more economical, in particular in respect of the capital costs and energy costs.

We have accordingly found a process for isolating pure tert-butyl (meth)acrylate from crude tert-butyl (meth)acrylate by distillation, wherein the process is carried out in a dividing wall column (1) which has separation-active internals and vaporizer (7) and in which a dividing wall (8) is arranged in the longitudinal direction of the column to form an upper joint column region (9), a lower joint column region (14), an inflow section (10, 12) having a side feed point (2) and an offtake section (11, 13) having a side offtake point (3), the column has a number of theoretical plates in the range from 20 to 80, the side feed point (2) for the crude tert-butyl (meth)acrylate is arranged at a theoretical plate in the region commencing at least two theoretical plates above the bottommost theoretical plate and ending at least two theoretical plates below the uppermost theoretical plate, the side offtake point (3) for the pure tert-butyl (meth)acrylate is arranged at a theoretical plate in the region commencing at least two theoretical plates above the bottommost theoretical plate and ending at least two theoretical plates below the uppermost theoretical plate and the dividing wall (8) is arranged in the column in the region commencing at least one theoretical plate above the bottommost theoretical plate and ending at least one theoretical plate below the uppermost theoretical plate.

DETAILED DESCRIPTION OF THE INVENTION

Figure 1:
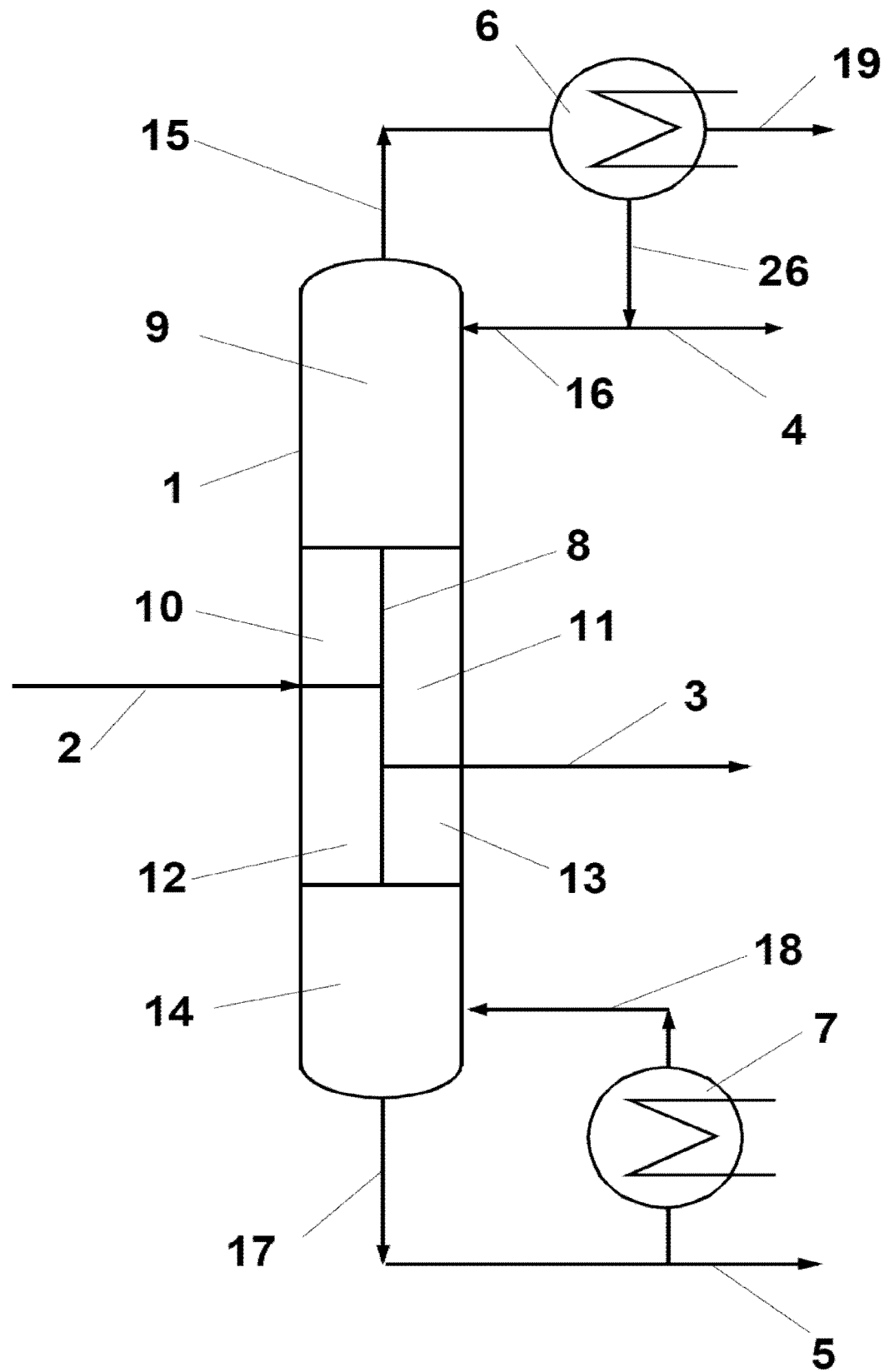
FIG. 1 illustrates an example of a dividing wall column according to the present application.

For the purposes of the present invention, pure tert-butyl (meth)acrylate is, in particular, a tert-butyl (meth)acrylate having a purity of ≥98.5% by weight, in particular ≥99.5% by weight, of tert-butyl acrylate or tert-butyl methacrylate.

For the purposes of the present invention, crude tert-butyl (meth)acrylate is, in particular, a mixture having a content of tert-butyl (meth)acrylate of from ≥30% by weight to ≤90% by weight, e.g. ≥40% by weight to ≤90% by weight, in particular from ≥55% by weight to ≤80% by weight.

The crude tert-butyl acrylate used in the process of the invention has, in particular, the following composition:

from 40 to 90% by weight, in particular from 55 to 80% by weight, of tert-butyl acrylate, from 0.1 to 50% by weight, in particular from 0.5 to 40% by weight, of acrylic acid, from 0.1 to 5% by weight, in particular from 0.5 to 4% by weight, of isobutene, from 0.1 to 5% by weight, in particular from 0.5 to 4% by weight, of diisobutene, from 0.1 to 5% by weight, in particular from 1 to 4% by weight, of relatively high boilers (relative to tert-butyl acrylate), from 0.1 to 5% by weight, in particular from 1 to 4% by weight, of further low boilers (relative to tert-butyl acrylate).

The crude tert-butyl methacrylate used in the process of the invention has, in particular, the following composition:

from 40 to 90% by weight, in particular from 55 to 80% by weight, of tert-butyl methacrylate, from 0.1 to 50% by weight, in particular from 0.5 to 40% by weight, of methacrylic acid, from 0.1 to 5% by weight, in particular from 0.5 to 4% by weight, of isobutene, from 0.1 to 5% by weight, in particular from 0.5 to 4% by weight, of diisobutene, from 0.1 to 5% by weight, in particular from 1 to 4% by weight, of relatively high boilers (relative to tert-butyl methacrylate), from 0.1 to 5% by weight, in particular from 1 to 4% by weight, of further low boilers (relative to tert-butyl methacrylate).

The process of the invention is carried out in a dividing wall column (1) in which a dividing wall (8) is arranged in the longitudinal direction of the column to form an upper joint column region (9), a lower joint column region (14), an inflow section (10, 12) and an offtake section (11, 13).

It has surprisingly been found that the isolation of pure tert-butyl (meth)acrylate from crude tert-butyl (meth)acrylate by distillation can, contrary to the assumption that a two-stage mode of operation at different pressures is necessary, be carried out in a single column, namely a dividing wall column, and thus at a uniform pressure.

A dividing wall column is a distillation column having a vertical dividing wall which, in subregions, prevents transverse mixing of liquid and vapor streams. The dividing wall, which generally consists of a flat metal sheet and can be welded, screwed or pushed in, divides the column in the longitudinal direction in its middle region into an inflow part and an offtake part. The mixture to be fractionated, namely the crude tert-butyl (meth)acrylate, is fed into the inflow section and the product, namely the pure tert-butyl (meth)acrylate, is taken off from the offtake section.

The process is preferably carried out continuously.

The dividing wall column is, like generally any distillation column, equipped with a vaporizer (bottom vaporizer) (7) and a condenser (6) at the top of the column.

In the process of the invention, the residence time in the vaporizer (7) and the associated piping system is advantageously and preferably limited to from 1 to 60 minutes, more preferably to from 10 to 30 minutes. This ensures trouble-free operation of the plant, in particular only little or no fouling, despite the polymerization susceptibility of the mixture.

In a preferred process variant, the ratio of the amount of liquid at the upper end of the dividing wall (8) going to the enrichment section (10) and the stripping section (11) of the column, i.e. amount to the enrichment section (10): amount to the stripping section (11), is set in the range from 1:0.2 to 1:5, i.e. from 5 to 0.2, preferably in the range from 1:0.5 to 1:2, i.e. from 2 to 0.5. This is preferably effected by the liquid being collected at the upper end of the dividing wall and being introduced via a regulating or adjusting device in the abovementioned ratio into the enrichment section and stripping section, respectively, of the column. This ensures a lower energy consumption.

In a further preferred process variant, the ratio of the amount of the vapor streams at the lower end of the dividing wall (8) going to the stripping section (12) and the enrichment section (13) of the column can also be set in addition to or as an alternative to regulation of the ratio of amounts of liquid runback at the upper end of the dividing wall (8). This is preferably effected by selection of the separation-active internals and/or by the additional installation of pressure drop-generating internals, for example orifice plates, or by regulation of the amounts of the vapor streams.

In a preferred process variant, the amounts of the vapor streams going to the stripping section (12) and the enrichment section (13) of the column, i.e. amount to stripping section (12):amount to enrichment section (13), is set in a ratio in the range from 1:0.5 to 1:2.0, i.e. from 2 to 0.5, preferably in a ratio in the range from 1:0.9 to 1:1.5, i.e. from 1/0.9 to 1/1.5.

The process of the invention is preferably carried out at a pressure at the top of the column of from 20 mbar to 5 bar, preferably from 50 to 200 mbar.

The upper joint column region (9) is preferably provided with temperature regulation supplying a temperature signal which can originate from a single measurement point or averaged over a plurality of measurement points below the uppermost theoretical plate, preferably at the third theoretical plate counted from the top, and utilizing as manipulated variable the distillate flow, the reflux ratio or preferably the amount of runback.

This ensures stable operation of the column, resulting in a further improvement in the achievable product purity.

In a further process variant, the lower column region is, in addition or as an alternative, provided with temperature regulation supplying a temperature signal which can originate from a single measurement point or averaged over a plurality of measurement points above the bottommost theoretical plate, preferably at the second theoretical plate counted from the bottom, and utilizing the amount taken off at the bottom as manipulated variable. A further improvement in stable column operation is achieved by means of this additional measure. Furthermore, it is possible, in addition or as an alternative, to provide level regulation which utilizes the amount taken off at the side as manipulated variable at the bottom of the column.

The ratio of the cross-sectional areas of the region of the offtake section (11, 13) to the region of the inflow section (10, 12) is preferably from 4:1 to 1:4, particularly preferably from 1.5:1 to 1:1.5, e.g. 1:1.

The dividing wall column (1) has a number of theoretical plates in the range from 20 to 80. Separation-active internals are present in the joint upper column region (9) and in the joint lower column region (14) and also in the inflow section (10, 12) and offtake section (11, 13).

The indication of the number of theoretical plates of the dividing wall column (1) always relates to the sum of the theoretical plates in the joint upper column region (9), the joint lower column region (14) and the inflow section (10, 12).

In general, the number of theoretical plates in the offtake section (11, 13) is the same as in the inflow section (10, 12), but can also be greater, e.g. greater by a factor of from 1 to 5, or smaller, e.g. smaller by a factor of from 1 to 5.

The side feed point (2) for the crude tert-butyl (meth) acrylate is arranged at a theoretical plate in the region commencing at least two theoretical plates above the bottommost theoretical plate and ending at least two theoretical plates below the uppermost theoretical plate, preferably at a theoretical plate in the region commencing at least five theoretical plates above the bottommost theoretical plate and ending at least five theoretical plates below the uppermost theoretical plate.

The side offtake point (3) for the pure tert-butyl (meth) acrylate is arranged at a theoretical plate in the region commencing at least two theoretical plates above the bottommost theoretical plate and ending at least two theoretical plates below the uppermost theoretical plate, preferably in the region commencing at least five theoretical plates above the bottommost theoretical plate and ending at least five theoretical plates below the uppermost theoretical plate.

The dividing wall (8) is arranged in the column in the region commencing at least one theoretical plate above the bottommost theoretical plate and ending at least one theoretical plate below the uppermost theoretical plate, preferably in the region commencing at least four theoretical plates above the bottommost theoretical plate and ending at least four theoretical plates below the uppermost theoretical plate, particularly preferably in each case centrally.

In a particularly preferred embodiment, the dividing wall column (1) has a number of theoretical plates in the range from 30 to 40, the side feed point (2) for the crude tert-butyl (meth)acrylate is arranged at a theoretical plate in the region commencing at least 12 theoretical plates above the bottommost theoretical plate and ending at least six theoretical plates below the uppermost theoretical plate, the side offtake point (3) for the pure tert-butyl (meth)acrylate is arranged at a theoretical plate in the region commencing at least 10 theoretical plates above the bottommost theoretical plate and ending at least 10 theoretical plates below the uppermost theoretical plate and the dividing wall (8) in the column is arranged in the region commencing at least five theoretical plates above the bottommost theoretical plate and ending at least five theoretical plates below the uppermost theoretical plate.

In the case of equal numbers of theoretical plates in the offtake section (11, 13) and the feed section (10, 12), the side offtake point (3) can be located either at the same theoretical plate as the side feed point (2) or else below or above the side feed point; however self-evidently in each case on the other side of the dividing wall (8) (cf. FIG. 1); the opposite side offtake point (3) is preferably located below, e.g. from one to 25, in particular from 2 to 20, very particularly preferably from 3 to 10, theoretical plates below, the side feed point (2). (The theoretical plates in the column or in the column region concerned or in the column section concerned are always counted from the bottom upward.)

In the case of different numbers of theoretical plates in the feed section (11, 13) and the inflow section (10, 12), the side having the greater total number of theoretical plates in the region of the dividing wall (8) is employed for counting the number of theoretical plates for establishing the relative height position of feed point and offtake point.

There are in principle no restrictions in respect of the separation-active internals; preference is given to random packing elements and/or ordered packing and/or trays being provided.

In a further preferred process variant, dual-flow trays are used as separation-active internals in the dividing wall column. The term dual-flow tray refers in a known manner to a column tray having openings through which vapor and liquid are passed in countercurrent.

In the thermal treatment of mixtures which comprise one or more polymerizable compounds in a column, there is always the problem that the column and the column internals are fouled by deposits and have to be cleaned in a complicated fashion, resulting in operation having to be interrupted. For the present purposes, the term thermal treatment refers to processes such as distillation or rectification, absorption, extraction or stripping. Mixtures which can be subjected to thermal treatment in a column are generally fluid, i.e. gaseous, liquid or gaseous/liquid.

The use of dual-flow trays reduces the fouling susceptibility of the dividing wall column compared to conventional tray columns. This increases the operating time of the column and thus makes it more economical.

Dual-flow trays are preferably used in the region of the dividing wall (10, 11, 12, 13); in a further preferred embodiment, dual-flow trays are also used in the joint upper column region (9) and in the joint lower column region (14).

A further advantageous embodiment provides for the use of dual-flow trays in the region of the dividing wall (10, 11, 12, 13) and in the joint lower column region (14) and also the use of random packing elements or ordered packing in the joint upper column region (9).

In WO 03/043712 A1 (BASF AG), it was shown for a conventional column without dividing wall that a considerable reduction in the fouling susceptibility and thus a considerably lengthening of the operating time of tray columns could be achieved by targeted selection of the diameters of the openings in the dual-flow trays.

In dividing wall columns, the same pressure drop prevails on both sides of the dividing wall. Precise setting of the gas distribution over the respective trays on the inflow side and on the offtake side by selection of the opening ratios of the trays on the inflow side and on the offtake side is of great advantage.

The gas distribution to the inflow side and the offtake side can be set precisely via targeted selection of the opening ratios. As a result of the different opening ratios of the dual-flow trays, different amounts of gas go to the two sides of the dividing wall at the same pressure drop. A complicated gas distribution facility below the dividing wall can thereby be dispensed with.

The opening ratio is set via the size and/or number of the openings. The opening ratio of a dual-flow tray is, as is known, the ratio of the sum of the areas of the openings and the total area of the dual-flow tray.

According to the invention, the openings of the dual-flow trays within a column can be made different, namely in that the diameter of the openings and/or the number of the openings are varied.

There is in principle no restriction in respect of the shape of the openings:

These can have any geometric shape, for example circles, ellipses, rectangles or polygons. The openings in the dual-flow trays are preferably circular.

A person skilled in the art can easily determine the required opening ratio as a function of gas and liquid loading and also opening diameter. The diameter of the openings in the dual-flow trays is preferably in the range from 10 to 80 mm, with dual-flow trays arranged above the feed point preferably having openings in the range from 10 to 50 mm and dual-flow trays arranged below the feed point, on the other hand, preferably having openings having diameters in the range from 15 to 80 mm.

The opening ratio of the dual-flow trays is preferably in the range from 10 to 30%.

In the process of the invention, the acrylic monomer, i.e. the tert-butyl (meth)acrylate, is preferably stabilized by means of suitable polymerization inhibitors in order to avoid undesirable polymerization. That is to say, the process of the invention is preferably carried out in the presence of effective amounts of a stabilizer or a plurality of stabilizers. Suitable stabilizers are in principle all polymerization inhibitors which are recommended for stabilizing (meth)acrylic acid and (meth)acrylic esters in, for example, DE 10 2005 053 982 A1 (BASF AG) and DE 102 58 329 A1 (BASF AG).

Suitable stabilizers can be, for example, N oxides (nitroxyl or N-oxyl radicals, i.e. compounds which have at least one >N—O group), e.g. 4-hydroxy-2,2,6,6-tetramethylpiperidin-N-oxyl or 4-oxo-2,2,6,6-tetramethylpiperidin-N-oxyl, phenols and naphthols such as p-methoxyphenol, p-aminophenol, p-nitrosophenol, 2-tert-butylphenol, 4-tert-butylphenol, 2,4-di-tert-butylphenol, 2-methyl-4-tert-butyl phenol, 2,6-tert-butyl-4-methylphenol or 4-tert-butyl-2,6-dimethylphenol, quinones such as hydroquinone or hydroquinone monomethyl ether, aromatic amines such as N,N-diphenylamine, phenylenediamines such as N,N'-dialkyl-p-phenylenediamine, where the alkyl radicals can be identical or different and can in each case have, independently of one another, from 1 to 4 carbon atoms and be linear or branched, e.g. N,N'-dimethyl-p-phenylenediamine or N,N'-diethyl-p-phenylenediamine, hydroxylamines such as N,N-diethylhydroxylamine, imines such as methylethylimine or methylene violet, sulfonamides such as N-methyl-4-toluenesulfonamide or N-tert-butyl-4-toluenesulfonamide, oximes such as aldoximes, ketoximes or amidoximes, e.g. diethyl ketoxime, methyl ethyl ketoxime or salicylaldoxime, phosphorus-comprising compounds such as triphenyl phosphine, triphenyl phosphite or triethyl phosphite, sulfur-comprising compounds such as diphenyl sulfide or phenothiazine, metal salts such as cerium(III) acetate or cerium (III) ethylhexanoate, or mixtures thereof.

The stabilization is preferably effected by means of phenothiazine (PTZ), p-methoxyphenol (MeHQ), hydroquinone, hydroquinone monomethyl ether, 4-hydroxy-2,2,6,6-tetramethylpiperidin-N-oxyl, 4-oxo-2,2,6,6-tetramethylpiperidin-N-oxyl, 2,6-tert-butyl-4-methylphenol or mixtures thereof.

Very particular preference is given to using phenothiazine (PTZ) and/or p-methoxyphenol (MeHQ) as polymerization inhibitor.

Even though the inhibitors can be added as pure substance, it is advantageous to add the inhibitor dissolved in a solvent as solution which can be metered in simply and reproducibly, with inhibitor mixtures in a single solution also being possible in principle. Preference is given to using a liquid which is in any case present in the acrylate synthesis process or the mixture of materials in the column as solvent. Particularly preferred choices for the solvent are the acrylate product itself (here tert-butyl acrylate or tert-butyl methacrylate) or one of the starting materials for the synthesis of the acrylate (here particularly acrylic acid or methacrylic acid).

The invention will be illustrated below with the aid of a drawing (FIG. 1) and an example.

The drawing shows, in the single figure, a dividing wall column 1 having a dividing wall 8 which divides the dividing wall column 1 into a joint upper column region 9, an inflow section 10 and 12 with enrichment section 10 and stripping section 12, an offtake section 11 and 13 with a stripping section 11 and an enrichment section 13, and also a joint lower column region 14. Separation-active internals are present in the column regions 9 and 14 and in the sections 10 to 13. The crude tert-butyl (meth)acrylate 2 enters the dividing wall column 1 between the column sections 10 and 12. The pure tert-butyl (meth)acrylate 3 is taken off between the column sections 11 and 13, preferably in liquid form. The vapor stream 15 obtained at the top of the column is partially condensed in the condenser 6, which is optionally supplemented by an after-condenser, and divided into the reflux stream 16 and the distillate stream 4. The uncondensed fraction from the condenser 6 comprises the low-boiling impurities and is taken off in vapor form as stream 19. At the lower end of the column, the liquid 17 is partially vaporized in a vaporizer 7 and recirculated via the pipe 18 into the column. A substream 5, which comprises the relatively high-boiling impurities, is taken off. The vaporizer 7 can be configured as a natural convection vaporizer or as forced circulation vaporizer; in the latter case, a circulation pump for the liquid stream 17 is additionally required. To avoid undesirable polymerization reactions, it is particularly advantageous to use a falling film evaporator instead of the forced circulation vaporizer since the shortest residence times are possible using such a falling film evaporator.

To reduce the residence time of the liquid in the vaporizer system, it is advantageous to arrange the level regulation not in the lower column cap but instead in the feed conduit for the liquid 17.

Figure 2:
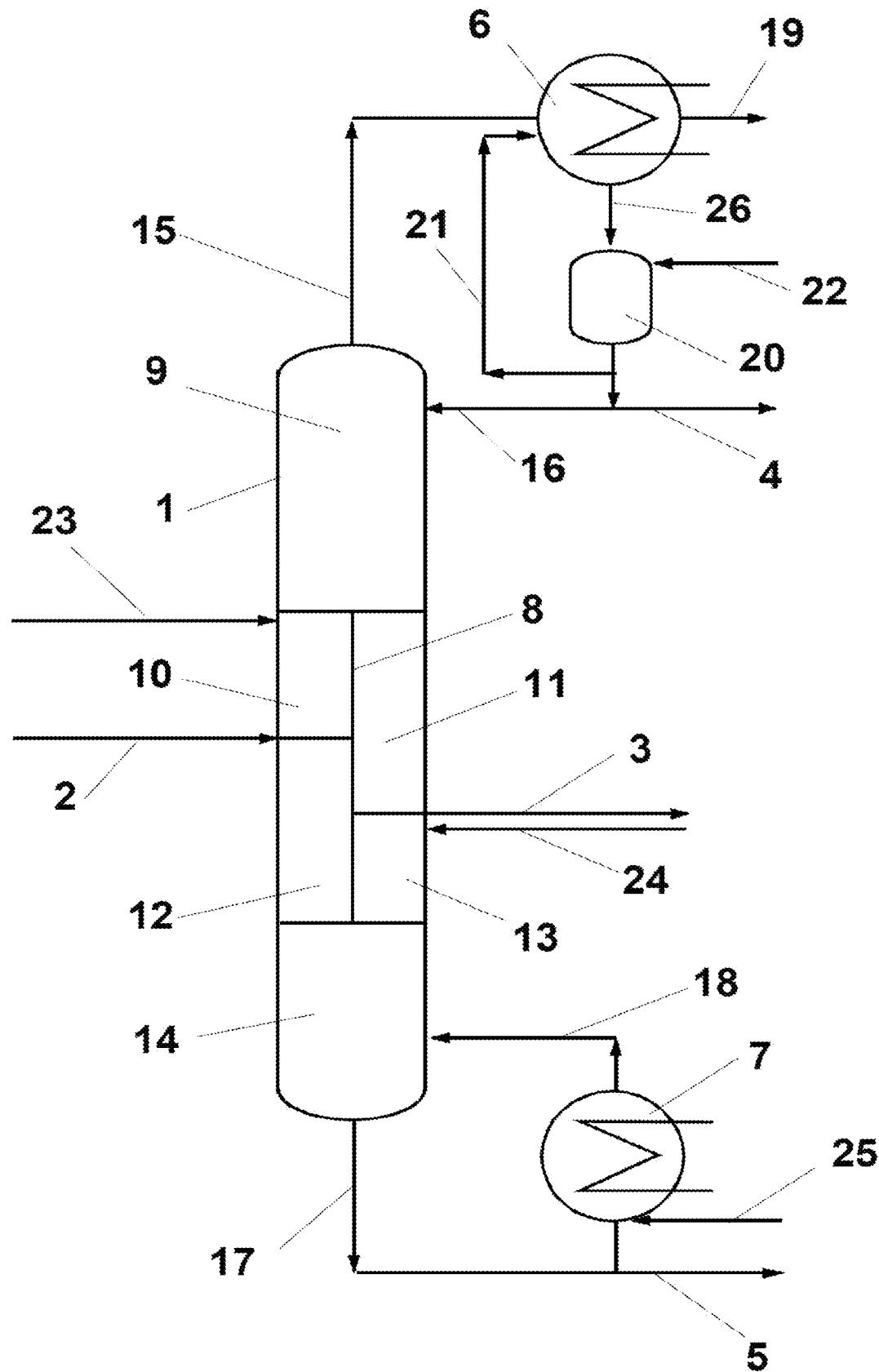
FIG. 2 illustrates a preferred mode of operation of the dividing wall column according to the present application.

In a preferred mode of operation (cf. FIG. 2), a stabilizer 1 (23) (process stabilizer; e.g. in particular PTZ) is introduced into the enrichment section (10) of the inflow section (10, 12), there in particular just below the upper end of the dividing wall (8), in the process of the invention. The stabilizer 1 can, in particular, be used as a solution in a suitable solvent, particularly a solvent as indicated above, e.g. tert-butyl acrylate or tert-butyl methacrylate. In this way, the entire inflow section (10, 12) and the joint lower part of the column (14) is stabilized by means of the process stabilizer. ("Just below the upper end of the dividing wall (8)" means, for example, "from one to 5 theoretical plates below the upper end of the dividing wall (8)").

Furthermore (cf. FIG. 2), a stabilizer 2 (22) (known as storage stabilizer, e.g. in particular MeHQ) is preferably introduced into the container (20) which collects the condensate (26) and/or into the conduit of a quenching circuit (21) and/or at the top of the condenser (6) in the process of the invention. The quenching circuit which is preferably provided (i.e. the liquid return stream of part of the condensate, e.g. from 10 to 50 hundredths by weight of the condensate, into the condenser (6)) has the function of particularly satisfactorily stabilizing the naturally stabilizer-free vapors (15) during condensation in the condenser (6). The joint upper column region (9) above the dividing wall (8) and also the feed section (10, 12) and offtake section (11, 13) in the region of the dividing wall are then stabilized by means of the stabilizer (in particular MeHQ) via the return line (16), with oxygen originating from lean air also being present. The introduction of lean air (25) (mixture of air and nitrogen, in particular in such a way that an oxygen content of from 4 to 9% by volume results) occurs in particular either at the lower end of the vaporizer (7) or at the lower end of the column (1).

In a further process variant (cf. FIG. 2), process stabilizer (24), in particular PTZ, is additionally introduced into the enrichment section (13) below the side offtake point (3).

All pressures indicated are absolute pressures.

All amounts in ppm are by weight (ppm by weight).

A "low boiler" (relative to tert-butyl (meth)acrylate) is a material whose boiling point is lower than the boiling point of the acrylate concerned, i.e. tert-butyl acrylate or tert-butyl methacrylate, at the same pressure.

A "relatively high boiler" (relative to tert-butyl (meth) acrylate) is a material whose boiling point is higher than the boiling point of the acrylate concerned, i.e. tert-butyl acrylate or tert-butyl methacrylate, at the same pressure.

EXAMPLES

The modes of operation are presented with the aid of data from a thermodynamic simulation of an overall plant for preparing tert-butyl acrylate.

The thermodynamic simulation of the process was carried out using the software Aspen Plus® (Aspen for short). Aspen is comprehensive simulation software which is used for the modeling, simulation and optimization of chemical processes and plants in industry. Aspen has comprehensive modeling data banks for modeling the basic operations and also materials data banks for the materials properties of many different substances. The properties of mixtures are calculated by Aspen by means of various thermodynamic models from the materials data of the pure substances.

Example 1

(Ratio of amount of liquid at the upper end of the dividing wall (8), enrichment section (10):stripping section (11)=1:3.4 and
ratio of amount of the vapor streams at the lower end of the dividing wall (8), stripping section (12):enrichment section (13)=1:1)

A crude tert-butyl acrylate stream of 2424 kg/h having a temperature of 24° C. was fed in in liquid form at the 20th theoretical plate of a dividing wall column (1) having a total of 38 theoretical plates. The crude tert-butyl acrylate had the following composition:
tert-Butyl acrylate: 68.3% by weight
Acrylic acid: 27.8% by weight
Isobutene: 1.0% by weight
Diisobutene: 1.4% by weight
tert-Butyl acetate: 0.1% by weight
Further relatively high boilers (relative to tert-butyl acrylate): balance The dividing wall (8) extended from the 8th to the 28th theoretical plate. The side offtake (3) was located at the 17th theoretical plate. The column was operated at a pressure at the top of 75 mbar and a pressure at the bottom of 223 mbar.

At the top of the column condensation was carried out at a temperature of 21° C. A gaseous low boiler-comprising stream (19) of 42 kg/h was taken off from the condenser (6). A substream (4) of 17 kg/h was taken off from the condensed stream. The high-boiling impurities (5) were taken off at the bottom of the column at a flow rate of 724 kg/h and a temperature of 97° C. At the side offtake, the desired product pure tert-butyl acrylate was obtained in liquid form at a temperature of 64° C. in an amount of 1640 kg/h.

The side offtake stream (3) had the following composition:
tert-Butyl acrylate: 99.93% by weight
Acrylic acid: <0.01% by weight
Isobutene: <0.01% by weight
Diisobutene: 0.06% by weight
tert-Butyl acetate: 8 ppm by weight
Further relatively high boilers (relative to tert-butyl acrylate): balance The minimum content of acrylate of >99.5% by weight and the commercial specifications for the secondary component tert-butyl acetate at 100 ppm are adhered to. The distillation yield for tert-butyl acrylate was more than 99%.

The ratio of amounts of liquid for the liquid at the upper end of the dividing wall (8), enrichment section (10): stripping section (11), was 1:3.4. At the lower end of the dividing wall (8), the amounts of vapor stream, stripping section (12):enrichment section (13), were divided in the ratio 1:1. The heating power of the vaporizer was 502 kW.

The process of the invention enabled the distillation of crude tert-butyl acrylate to give pure tert-butyl acrylate to be carried out, for example, at an annual capacity of 13 100 metric tons while adhering to the required specifications with a capital cost saving of 20% and an energy cost saving of 20% compared to a conventional two-stage distillation process.

Comparative Example 1

(Ratio of amount of liquid at the upper end of the dividing wall (8), enrichment section (10):stripping section (11)=1:7)

A crude tert-butyl acrylate stream of 2424 kg/h having a temperature of 24° C. was fed in in liquid form at the 20th theoretical plate of a dividing wall column (1) having a total of 38 theoretical plates. The crude tert-butyl acrylate had the following composition:
tert-Butyl acrylate: 68.3% by weight
Acrylic acid: 27.8% by weight
Isobutene: 1.0% by weight
Diisobutene: 1.4% by weight
tert-Butyl acetate: 0.1% by weight
Further relatively high boilers (relative to tert-butyl acrylate): balance The dividing wall (8) extended from the 8th to the 28th theoretical plate. The side offtake (3) was located at the 17th theoretical plate. The column was operated at a pressure at the top of 75 mbar and a pressure at the bottom of 223 mbar.

At the top of the column, condensation was carried out at a temperature of 21° C. A gaseous low boiler-comprising stream (19) of 42 kg/h was taken off from the condenser (6). A substream (4) of 17 kg/h was taken off from the condensed stream. The high-boiling impurities (5) were taken off at the bottom of the column at a flow rate of 724 kg/h and a temperature of 96° C. At the side offtake, the desired product pure tert-butyl acrylate was obtained in liquid form at a temperature of 65° C. in an amount of 1640 kg/h.

The side offtake stream (3) had the following composition:

tert-Butyl acrylate: 98.25% by weight
Acrylic acid: 1.70% by weight
Isobutene: <0.01% by weight
Diisobutene: 0.04% by weight
tert-Butyl acetate: 7 ppm by weight The minimum content of acrylate of >99.5% by weight is not adhered to.

The distillation yield for tert-butyl acrylate was more than 97%.

The ratio of amounts of liquid for the liquid at the upper end of the dividing wall (8), enrichment section (10):stripping section (11), was 1:7. At the lower end of the dividing wall (8), the amounts of vapor stream, stripping section (12):enrichment section (13), were divided in the ratio 1:1. The heating power of the vaporizer was 500 kW.

Comparative Example 2

(Ratio of amounts of the vapor streams at the lower end of the dividing wall (8), stripping section (12):enrichment section (13)=3:1)

A crude tert-butyl acrylate stream of 2424 kg/h having a temperature of 24° C. was fed in in liquid form at the 20th theoretical plate of a dividing wall column (1) having a total of 38 theoretical plates. The crude tert-butyl acrylate had the following composition:
tert-Butyl acrylate: 68.3% by weight
Acrylic acid: 27.8% by weight
Isobutene: 1.0% by weight
Diisobutene: 1.4% by weight
tert-Butyl acetate: 0.1% by weight
Further relatively high boilers (relative to tert-butyl acrylate): balance The dividing wall (8) extended from the 8th to the 28th theoretical plate. The side offtake (3) was located at the 17th theoretical plate. The column was operated at a pressure at the top of 75 mbar and a pressure at the bottom of 223 mbar.

At the top of the column, condensation was carried out at a temperature of 21° C. A gaseous low boiler-comprising stream (19) of 42 kg/h was taken off from the condenser (6). A substream (4) of 7 kg/h was taken off from the condensed stream. The high-boiling impurities (5) were taken off at the bottom of the column at a flow rate of 734 kg/h and a temperature of 96° C. At the side offtake, the desired product pure tert-butyl acrylate was obtained in liquid form at a temperature of 64° C. in an amount of 1640 kg/h.

The side offtake stream (3) had the following composition:
tert-Butyl acrylate: 98.11% by weight
Acrylic acid: 1.29% by weight
Isobutene: <0.01% by weight
Diisobutene: 0.58% by weight
tert-Butyl acetate: 158 ppm by weight The minimum content of acrylate of >99.5% by weight and the commercial specification for the secondary component tert-butyl acetate are not adhered to.

The distillation yield for tert-butyl acrylate was more than 97%.

The ratio of amounts of liquid for the liquid at the upper end of the dividing wall (8), enrichment section (10):stripping section (11), was 1:3.5. At the lower end of the dividing wall (8), the amounts of vapor stream, stripping section (12):enrichment section (13), were divided in the ratio 3:1. The heating power of the vaporizer was 500 kW.

The invention claimed is:

1. A process, comprising:
   isolating pure tert-butyl (meth)acrylate from crude tert-butyl (meth)acrylate by distillation,
   wherein the crude tert-butyl (meth)acrylate is obtained from reacting isobutene with (meth)acrylic acid,
   wherein the process is carried out in a dividing wall column comprising:
     separation-active internals;
     a vaporizer; and
     a dividing wall, which is arranged in a longitudinal direction of the dividing wall column to form an upper joint column region, a lower joint column region, an inflow section having a side feed point for the crude tert-butyl (meth)acrylate, and an offtake section having a side offtake point for the pure tert-butyl (meth)acrylate,
   wherein the dividing wall column has from 20 to 80 theoretical plates in the joint upper column region, the joint lower column region, and the inflow section combined,
   wherein the side feed point for the crude tert-butyl (meth)acrylate is arranged at a theoretical plate in a region commencing at least two theoretical plates above a bottommost theoretical plate and ending at least two theoretical plates below an uppermost theoretical plate,
   wherein the side offtake point for the pure tert-butyl (meth)acrylate is arranged at a theoretical plate in the region commencing at least two theoretical plates above the bottommost theoretical plate and ending at least two theoretical plates below the uppermost theoretical plate
   wherein the dividing wall is arranged in the dividing wall column in a region commencing at least one theoretical plate above the bottommost theoretical plate and ending at least one theoretical plate below the uppermost theoretical plate,
   wherein the ratio of amounts of liquid at an upper end of the dividing wall going to an enrichment section and a first stripping section of the dividing wall column is set in a range of from 1:0.2 to 1:5,
   wherein the ratio of amounts of vapor streams at a lower end of the dividing wall going to a second stripping section and an enrichment section of the dividing wall column is set in a range of from 1:0.5 to 1:2.0, and
   wherein there are dual-flow trays on the inflow side and offtake side, and the dual-flow trays on the inflow side and offtake side have different opening ratios for setting an optimal gas distribution over the two sides of the dividing wall.

2. The process of claim 1, wherein the side feed point for the crude tert-butyl (meth)acrylate is arranged at a theoretical plate in a region commencing at least five theoretical plates above the bottommost theoretical plate and ending at least five theoretical plates below the uppermost theoretical plate,
   wherein the side offtake point for the pure tert-butyl (meth)acrylate is arranged at a theoretical plate in the region commencing at least five theoretical plates above the bottommost theoretical plate and ending at least five theoretical plates below the uppermost theoretical plate, and
   wherein the dividing wall in the dividing wall column is arranged in a region commencing at least four theoretical plates above the bottommost theoretical plate and ending at least four theoretical plates below the uppermost theoretical plate.

3. The process of claim 1, wherein the dividing wall column has from 30 to 40 theoretical plates in the joint upper column region the joint lower column region, and the inflow section combined,
  wherein the side feed point for the crude tert-butyl (meth) acrylate is arranged at a theoretical plate in a region commencing at least 12 theoretical plates above the bottommost theoretical plate and ending at least six theoretical plates below the uppermost theoretical plate,
  wherein the side offtake point for the pure tert-butyl (meth)acrylate is arranged at a theoretical plate in a region commencing at least 10 theoretical plates above the lowermost theoretical plate and ending at least 10 theoretical plates below the uppermost theoretical plate, and
  wherein the dividing wall in the dividing wall column is arranged in a region commencing at least five theoretical plates above the bottommost theoretical plate and ending at least five theoretical plates below the uppermost theoretical plate.

4. The process of claim 1, wherein the side offtake point is located at least one theoretical plate below the side feed point, with the proviso that when there are different numbers of theoretical plates in the offtake section and the inflow section, the side having the greatest total number of theoretical plates in the region of the dividing wall is employed for counting the number of theoretical plates for determining a relative height position of feed point and offtake point.

5. The process of claim 1, wherein the residence time in the vaporizer and an associated piping system is limited to from 1 to 60 minutes.

6. The process of claim 1, wherein the ratio of amounts of liquid at the upper end of the dividing wall going to the enrichment section and the stripping section of the dividing wall column is set in the range from 1:0.5 to 1:2.

7. The process of claim 1, wherein the ratio of amounts of vapor streams at the lower end of the dividing wall going to the second stripping section and the enrichment section of the dividing wall column is set in a range of from 1:0.9 to 1:1.5.

8. The process of claim 1, wherein a pressure at the top of the dividing wall column is in the range of from 20 mbar to 5 bar.

9. The process of claim 1, wherein a temperature signal below the uppermost theoretical plate, which utilizes the distillate flow, the reflux ratio or the amount of reflux as a manipulated variable, is used to regulate temperature in the upper joint column region.

10. The process of claim 1, wherein a temperature signal above the bottommost theoretical plate, which utilizes the amount taken off at the bottom of the dividing wall column as a manipulated variable, is used to regulate temperature in the lower joint column region.

11. The process of claim 1, wherein there is level regulation at the bottom of the dividing wall column which utilizes the amount taken off at the side of the dividing wall column as a manipulated variable.

12. The process of claim 1, wherein the ratio of cross-sectional areas of the region of the offtake section and the region of the inflow section is from 4:1 to 1:4.

13. The process of claim 1, wherein the ratio of cross-sectional areas of the region of the offtake section and the region of the inflow section is from 1.5:1 to 1:1.5.

14. The process of claim 1, wherein the pure tert-butyl (meth)acrylate has a purity of ≥98.5%.

15. The process of claim 1, wherein the tert-butyl (meth) acrylate is tert-butyl acrylate.

16. The process of claim 1, wherein the tert-butyl (meth) acrylate is tert-butyl methacrylate.

17. The process of claim 15, wherein the crude tert-butyl acrylate has the following composition:
  from 40 to 90% by weight of tert-butyl acrylate;
  from 0.1 to 50% by weight of acrylic acid;
  from 0.1 to 5% by weight of isobutene;
  from 0.1 to 5% by weight of diisobutene;
  from 0.1 to 5% by weight of relatively high boilers (relative to tert-butyl acrylate); and
  from 0.1 to 5% by weight of further low boilers (relative to tert-butyl acrylate).

18. The process of claim 16, wherein the crude tert-butyl methacrylate has the following composition:
  from 40 to 90% by weight of tert-butyl methacrylate;
  from 0.1 to 50% by weight of methacrylic acid;
  from 0.1 to 5% by weight of isobutene;
  from 0.1 to 5% by weight of diisobutene;
  from 0.1 to 5% by weight of relatively high boilers (relative to tert-butyl methacrylate); and
  from 0.1 to 5% by weight of further low boilers (relative to tert-butyl methacrylate).

19. The process of claim 1, wherein a stabilizer is introduced into the enrichment section of the inflow section.

20. The process of claim 19, wherein the stabilizer is phenothiazine.

21. The process of claim 1, wherein the dividing wall column further comprises a condenser and a container that collects a condensate, and
  wherein a stabilizer is introduced into the container and/or into a conduit of a quenching circuit, where this is a liquid return stream of part of the condensate into the condenser, and/or at the top of the condenser.

22. The process of claim 21, wherein the stabilizer is p-methoxyphenol.

* * * * *

UNITED STATES PATENT AND TRADEMARK OFFICE
CERTIFICATE OF CORRECTION

PATENT NO. : 10,730,823 B2  
APPLICATION NO. : 16/471993  
DATED : August 4, 2020  
INVENTOR(S) : Ortmund Lang et al.

Page 1 of 1

It is certified that error appears in the above-identified patent and that said Letters Patent is hereby corrected as shown below:

On the Title Page

In Column 2, item (56), Other Publications, Line 1, "(Scientia" should read -- Scientia --.

In Column 2, item (56), Other Publications, Line 4, "16/062,369" should read -- 16/062,359 --.

In Column 2, item (56), Other Publications, Lines 19-20, "Moglichkeiten zur Proze integration bei destillativen Trennverfahren" should read -- Möglichkeiten zur Prozessintegration bei destillation Trennverfahren --.

In the Specification

In Column 1, Line 23 (approx.), "Not Applicable" should read -- Not Applicable. --, in Column 1, Line 24, as the continuation of next paragraph.

In Column 7, Line 6, "openings:" should read -- openings. --.

In the Claims

In Column 13, Line 3, Claim 3, "region" and insert -- region, --.

Signed and Sealed this  
Second Day of February, 2021

Drew Hirshfeld  
*Performing the Functions and Duties of the*  
*Under Secretary of Commerce for Intellectual Property and*  
*Director of the United States Patent and Trademark Office*